United States Patent
Behrends et al.

(10) Patent No.: US 8,541,454 B2
(45) Date of Patent: Sep. 24, 2013

(54) ANTISEPTIC BASED ON BISPYRIDINIUM ALKANES

(75) Inventors: Sabine Behrends, Appen (DE); Andreas Dettmann, Hamburg (DE); Mona Golombiewski, Luneburg (DE); Elke Kassens, Grabau (DE)

(73) Assignee: L'Air Liquide, Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 0 days.

(21) Appl. No.: 13/156,635

(22) Filed: Jun. 9, 2011

(65) Prior Publication Data

US 2012/0004593 A1  Jan. 5, 2012

(30) Foreign Application Priority Data

Jul. 2, 2010  (DE) .......................... 10 2010 025 932

(51) Int. Cl.
*A01N 43/40* (2006.01)
*A61K 31/4425* (2006.01)

(52) U.S. Cl.
USPC ..... 514/332; 514/334; 424/70.31; 424/70.28; 424/417

(58) Field of Classification Search
USPC .................. 514/332, 334; 424/70.31, 70.28, 424/417
See application file for complete search history.

(56) References Cited

U.S. PATENT DOCUMENTS

| 2006/0165612 A1* | 7/2006 | Beilfuss et al. ................. 424/49 |
| 2009/0076084 A1 | 3/2009 | Krug et al. |
| 2011/0003857 A1 | 1/2011 | Beilfuss et al. |

FOREIGN PATENT DOCUMENTS

| DE | 2708 331 | 9/1977 |
| DE | 196 47 692 | 6/1998 |
| DE | 102 05 883 | 8/2003 |
| DE | 10 2005 002 644 | 7/2006 |
| DE | 10 2005 058 978 | 3/2007 |
| DE | 10 2005 063 375 | 4/2007 |
| DE | 10 2008 011 691 | 9/2009 |
| DE | 10 2008 011 692 | 9/2009 |
| EP | 0 411 315 | 2/1991 |
| EP | 1 982 696 | 10/2008 |
| EP | 2 201 951 | 6/2010 |

OTHER PUBLICATIONS

Schulke & Mayr, Octenivet Solution. Preparation Information Wound Treatment in Animals, Norderstedt, Jun. 2010 URL: http://www.schuelke.com/download/pdf/cde_ide-_octenivet_Loesung_prod.pdf.
German Office Action, dated Feb. 24, 2010, from corresponding German application.

* cited by examiner

*Primary Examiner* — Savitha Rao
(74) *Attorney, Agent, or Firm* — Young & Thompson

(57) ABSTRACT

An antimicrobially effective composition includes a) at least 0.15% by weight of bispyridinium alkane, b) at least 3.5% by weight of humectant and c) water. Upon dilution with water, the composition produces a solution with an osmolality of from 230 to 350 mOsmol/kg and is free from surfactant. It is used as an antiseptic and is suitable for use in a method for the disinfection of injured or uninjured skin of a human being or animal, preference being given to use in the case of newborns, in particular those born prematurely.

13 Claims, No Drawings

ANTISEPTIC BASED ON BISPYRIDINIUM ALKANES

The present invention relates to an antimicrobially effective composition based on bispyridinium alkanes such as octenidine dihydrochloride, and to the use of the composition as antiseptic.

Antiseptics based on bispyridinium alkanes are known. Bispyridinium alkanes are active ingredients, which are characterized by high efficacy coupled with low resorption on wounds. For example, EP 0 411 315 A1 discloses an aqueous antiseptic composition which comprises octenidine dihydrochloride and phenoxyethanol and/or phenoxypropanol in a specific weight ratio. Octenidine dihydrochloride (referred to below as octenidine) is a quaternary ammonium compound, and specifically a bispyridinium alkane, with the following structure:

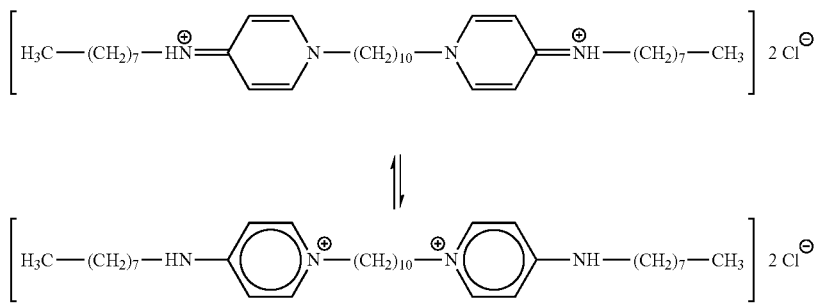

The compositions according to DE 196 47 692 A1 comprise octenidine, $C_1$- to $C_8$-alkyl alcohol, non-ionic and/or cationic surfactant and skin-compatible α-hydroxy carboxylic acid and are used as washing hand disinfectant.

Furthermore, the product Octenisept™ has been successfully sold for many years by Schülke & Mayr GmbH, Norderstedt, Federal Republic of Germany, as mucosa and wound antiseptic. Octenisept™ comprises inter alia 0.1% by weight of octenidine, 2% by weight of phenoxyethanol and cocamidopropylbetaine as amphoteric surfactant, in aqueous solution.

EP 1 982 696 A1 discloses antiseptic gels based on a specific poloxamer. Poloxamers are non ionic surfactants and are prepared by copolymerizing propylene oxide with ethylene oxide. The gels comprise octenidine and/or polyhexanide as active ingredient and are characterized by an increase in the viscosity in the range from 20° C. to 30° C.

The aqueous antiseptic according to DE 102 05 883 A1 comprises octenidine and non ionic surfactant selected from alcohol polyalkoxylates, polysorbates and alkyl glycosides. It is free from alcohols and can be both rendered isotonic and also diluted with salt solutions to give isotonic solutions without resulting in precipitations. As explained in DE 102 05 883 A1, precipitations in an antiseptic that has been rendered isotonic are undesired, because they lead to hypo- or hypertonic solutions or to a change in the active ingredient content. In addition, aqueous solutions are known as wound-rinsing solutions which comprise octenidine, glycerol and ethylhexyl glycerol ether. They are isotonic and free from alcohol and dyes.

DE 10 2005 063 375 A1 discloses antimicrobial preparations which comprise octenidine encapsulated in liposomes and are preferably in the form of a solution, dispersion, cream, ointment, gel or suppository. They are used for the treatment of wounds, infected eczema, mycoses and vaginal infections.

DE 10 2008 011 692 A1 relates to an active ingredient combination which comprises:

(a) Glycerol monoalkyl ethers, such as, for example, ethylhexyl glycerol ether, as non ionic surfactant, (b) Bispyridinium alkane, such as, for example, octenidine, (c) Polyol, such as, for example, 1,2-propylene glycol and (d) Antioxidant.

The combination is advantageously used for producing a preparation for the treatment of undesired body odour, for example for producing a cosmetic deodorant preparation, an antidandruff hair cleanser, a preparation for the treatment of bad skin and acne or a preparation for the treatment of foot and/or skin fungus.

DE 10 2005 058 978 A1 relates to an aqueous wound and mucosa disinfectant which comprises:

(a) Octenidine, (b) One or more active ingredients selected from the group consisting of ethanol, 1-propanol, 2-propanol, undecyleneamidopropyltrimonium methosulphate, 3-(4-chloro phenoxy) 1,2-propanediol and/or sodium hydroxymethylglycinate, (c) Glycerol and/or 1,2-diols having 3 to 10 carbon atoms, and (d) optionally surfactants, emulsifiers, solubility promoters, pH regulators, dyes, perfumes and/or thickeners, the composition being free from phenoxyethanol, phenoxypropanol, phenoxyisopropanol and organic acids.

DE 102 05 883 A1 relates to an alcohol-free, aryloxy alcohol-free antiseptic which comprises 0.01% to 10% by weight of bispyridinium alkane, in particular octenidine, and 0.01% to 20% by weight of non ionic surfactant, selected from alcohol polyalkoxylates, polysorbates and alkyl glycosides, and also optionally one or more auxiliaries, and to its use as skin disinfectant or rinse solution for antiseptic measures for skin, mucosa, wounds or internal organs.

The known antiseptics are associated with disadvantages.

Antiseptics which necessarily require the presence of alcohols (for example aliphatic alcohols such as ethanol, propanol or butanol or aromatic alcohols such as benzyl alcohol, phenoxyethanol or phenoxypropanol) should be avoided on account of potential allergic reactions.

Antiseptics with a content of (cationic, anionic, non ionic and/or amphoteric) surfactant as secondary constituent likewise harbour the risk of an allergy potential and can lead to severe undesired foam formation, for example in the case of ultrasound-associated wound treatment (UAW).

In addition, bispyridinium alkanes, such as, for example, octenidine, often have inadequate stability in the presence of non ionic surfactants, which demands the addition of antioxidants. However, antioxidants are undesired in antiseptics, especially in sensitive areas of application such as, for example, use for the disinfection of the sensitive skin of a newborn, in particular premature, human being or animal.

Moreover, it should be possible to formulate compositions for antisepsis isotonically, as is already described in DE 102 05 883 A1. Solutions isotonic to blood plasma comprise dissolved particles in a concentration of 290 mOsmol/kg, e.g. 0.9% by weight aqueous NaCl solution. The isotonicity of antiseptics is usually adjusted using inorganic salts, as are present in Ringer's solution and NaCl solution. However, in the case of antiseptics which are rendered isotonic with the help of inorganic salts such as NaCl or Ringer's solution, there is always the risk of precipitations during storage, especially at a low temperature.

Ultimately, antiseptics are undesired which comprise large amounts of active ingredient and/or two or more active ingredients for satisfactory antimicrobial efficacy, or which comprise one or more secondary constituents, since this is associated with the risk that the composition cannot be used in patients who cannot tolerate just one of the active ingredients or secondary constituents. Consequently, antiseptics should only comprise the ingredients that are absolutely necessary for the application. This is true particularly for application on the sensitive skin of a newborn, in particular premature, human being or animal.

The object of the present invention was therefore to provide a composition for use as antiseptic, for example wound and mucosa antiseptic. The composition should be suitable in particular for use in a method for the disinfection of the sensitive skin of a newborn, in particular premature, human being or animal. The composition should not automatically require the presence of surfactant for good wettability, of alcohol for good efficacy, of inorganic salts for isotonicity and/or of antioxidants for good storability. The compositions should be stable over a broad temperature range, i.e. not have a tendency towards separation of constituents (for example precipitations). Finally, the compositions should be easy to produce.

Surprisingly, it has now been found that this object is achieved by an antimicrobially effective composition which comprises:
  a) At least 0.15% by weight of bispyridinium alkane,
  b) At least 3.5% by weight of humectant and
  c) Water.

The composition according to the invention produces:
  (i) Upon dilution with water, a solution with an osmolality of from 230 mOsmol/kg to 350 mOsmol/kg.

Since the osmotic pressure in a solution behaves proportionally to the depression in the freezing point of a solution, the osmolality can be determined in accordance with the principle of freezing point depression. This determination can be carried out, for example, using a semimicro-osmometer from Knauer. It is done according to a normalized method based the European Pharmacopea (Ph. Eur. 6.0.,2.2.35 osmolality)

In addition, the composition:
  (ii) is free from surfactant. The obligatorily prescribed bispyridinium alkane of component a) is not considered to be a surfactant for the purposes of the description of the present invention. "Surfactant-free" thus means, that the composition according to the invention comprises no anionic, cationic, non ionic or amphoteric surfactant besides the one or, if appropriate, more bispyridinium alkanes.

In one particularly preferred embodiment, no anionic, cationic, non ionic or amphoteric surfactant—apart from octenidine—is present in the composition according to the invention. In the present application, glycerol monoalkyl ethers, such as, for example, ethylhexyl glycerol ether, are regarded as surfactants.

The invention is based inter alia on the fact that it has been found that the solution with an osmolality of from 230 mOsmol/kg to 350 mOsmol/kg, i.e. the use solution which is produced upon diluting the composition with water, has an adequate efficacy for antisepsis, in particular wound and mucosa antisepsis, even in the absence of (aliphatic and aromatic) alcohols. Through the physiological pH, the octenidine that is classed as toxicologically acceptable as active ingredient and the omission of surfactants and further substances in the use solution that are not necessarily required for the antimicrobial efficacy, a very compatible composition is provided which is stable in all climatic zones and which has an improved storage time of at least 12 months compared with antiseptics from the prior art. Moreover, the composition can be sterilized. Furthermore, the composition is a concentrate, which is associated with advantages in terms of transportation (lower transport costs).

A further surprising property of the compositions according to the invention is their ability to be adjusted to blood isotonicity through dilution with water. This effect is based on the action of the humectant as isotonicity agent. Keeping a wound moist is essential for good wound healing. Consequently, it is possible to dispense with the addition of inorganic salts for adjusting the isotonicity, as are present e.g. in isotonic sodium chloride solution and Ringer's solution. This ensures firstly very good tolerability and, secondly, improved stability of the use solutions since an addition of inorganic salts, in particular in combination with octenidine, can lead to the formation of crystalline precipitates. In addition, in contrast to antiseptics known from the prior art and based on bispyridinium alkanes, such as in particular octenidine-containing antiseptics, the isotonicity of which has been adjusted by means of inorganic salts, there is no inhibition of the antimicrobial efficacy in the use solutions produced by dilution with water.

It was surprising, for example, that in use solutions the known good efficacy of octenidine is adversely affected by the addition of surfactants such as e.g. cocamidopropylbetaine, as shown in Example 5 below. An additional benefit of omitting the surfactant thus consists in significantly better tolerability (lower allergenic potential).

A particularly preferred composition according to the invention is:
  (iii) Free from alcohol. Thus, in particular the presence of aliphatic alcohols such as ethanol, propanol or butanol, and aromatic alcohols such as benzyl alcohol, phenoxyethanol or phenoxypropanol, as are present in numerous antiseptics according to the prior art, is excluded.

In addition, a preferred composition according to the invention is:
  (iv) Free from inorganic salts, for example those salts which are customary for the formulation of isotonic compositions (Ringer's solutions, sodium chloride solutions). In this connection, inorganic salt is intended to mean a salt of both inorganic cation and inorganic anion, i.e. salts of bispyridinium alkanes with (inorganic) anions are not considered to be inorganic salts.

In addition, a preferred composition according to the invention is:
  (v) Free from antioxidant.

Preferably, the osmolality of the composition according to the invention upon dilution is 250 mOsmol/kg to 330 mOsmol/kg, more preferably 260 mOsmol/kg to 320 mOsmol/kg, in particular 270 mOsmol/kg to 310 mOsmol/kg.

Preferably, the dilution of the composition according to the invention takes place by diluting 1 part by weight of composition with water to 2 parts to 20 parts by weight, more preferably 3 parts to 10 parts by weight, even more preferably 4 parts to 7 parts by weight, such as for example 5 parts by weight. Typically, the dilution takes place with water which has a water quality monographed in the European Pharmacopoeia (Ph. Eur.), in particular with Aqua purificata Ph. Eur. (purified water) or Aqua ad injectabilia Ph. Eur. (water for injection purposes).

a) Bispyridinium Alkane

The term bispyridinium alkane encompasses the bis[4-(substituted-amino)-1-pyridinium] alkanes, disclosed in DE 2708 331 C2, of the general formulae (I) or (II)

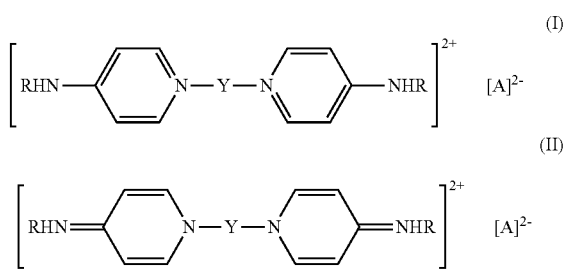

In which

Y is an alkylene group having 4 to 18 carbon atoms,

R is an alkyl group having 6 to 18 carbon atoms or a cycloalkyl group having 5 to 7 carbon atoms or the phenyl radical, which is substituted by a halogen atom, and A is one or more anions.

Strictly speaking, the aforementioned definition of A applies for mono- and divalent anions, although A can of course also be a polyvalent anion, e.g. phosphate or orthosilicate. Furthermore, the term bispyridinium alkane includes the various prototropes of the compounds of the formula (I), as is disclosed, for example, in DE 196 47 692 A1.

In all embodiments of the invention, however, it is preferred that component a) is octenidine dihydrochloride (R=n-octyl, Y=n-decenyl; A=2×Cl).

Preferred amounts of component a) in the composition according to the invention are 0.15% to 10% by weight, preferably 0.15% to 8% by weight, more preferably 0.15% to 5% by weight, even more preferably 0.2% to 2.5% by weight, in particular 0.25% to 1% by weight, most preferably 0.4% to 0.6% by weight, such as about 0.5% by weight.

b) Humectant

Preferred humectants are selected from the group of polyhydric alcohols and mixtures thereof, preferably glycerol, 1,2-propylene glycol, sorbitol, glucose, fructose, glucuronic acid, lactose, lactic acid, lactates, lactulose, polyethylene glycols, sucrose, hyaluronic acid, xylitol, xylose and mixtures thereof.

It is particularly preferred that component b) is glycerol.

Preferred amounts of component b), in particular glycerol, are 3.5% to 40% by weight, preferably 4% to 30% by weight, more preferably 5% to 20% by weight, even more preferably 7.5% to 17.5% by weight, in particular 10% to 15% by weight, most preferably 11% to 13% by weight, such as 11.5% to 12.5% by weight, such as about 12.1% by weight.

Consequently, particular preference is given to a composition which consists of the components:

a) Octenidine dihydrochloride, preferably in an amount of from 0.25% to 1% by weight, b) Glycerol, preferably in an amount of from 11% to 13% by weight, and c) Water as the remainder and upon dilution with water produces an osmolality of from 270 mOsmol/kg to 310 mOsmol/kg.

Antimicrobially effective compositions according to the invention are suitable for use in a method for the disinfection of injured or uninjured skin of a human being or animal. In the disinfection method, the compositions are diluted prior to use as antiseptic with water to use solutions with an osmolality of from 230 mOsmol/kg to 350 mOsmol/kg. The dilution of the composition in order to obtain a use solution, and the application of the use solution, can be carried out by different people. For example, the dilution can take place in a hospital pharmacy and the application can be carried out by a doctor or a nurse.

Preferably, the injured or uninjured skin in all embodiments of the invention is a wound or mucosa.

In addition, the injured or uninjured skin is preferably the skin of a newborn human being or animal, in particular of a premature human being or animal. In the present application, a newborn human being is intended to mean a child from birth to the age of four weeks. In addition, in the present application, a premature human being is intended to mean a newborn human being produced from a pregnancy lasting less than 37 complete weeks. The present definition of a premature human being therefore also includes a very small premature human being (VLBW, Very Low Birth Weight) who, at birth, weighs less than 1500 g and as a rule is produced from a pregnancy lasting less than 32 complete weeks. The use solution is suitable in particular for the skin of VLBW newborns.

The disinfection method can encompass an ultrasound-associated wound treatment (UAW) in all embodiments of the invention.

Through dilution with water, from the composition according to the invention it is possible to produce an antimicrobially effective use solution which comprises:

a) 0.001% to 1% by weight of bispyridiniumalkane, b) Humectant and c) Water, where the use solution (i) has an osmolality of from 230 mOsmol/kg to 350 mOsmol/kg and (ii) is free from surfactant.

The use solution is suitable for use in a method for the disinfection of injured or uninjured skin of a newborn human being or animal, in particular of a premature human being or animal. Examples of animals for which the use solution can be used are all vertebrates in all embodiments of the invention.

For use in the disinfection method, of particular suitability is a use solution which consists of the components:

a) Octenidine dihydrochloride, preferably in an amount of from 0.05% to 0.2% by weight, b) Glycerol, preferably in an amount of from 2.2% to 2.6% by weight, and c) Water as the remainder and has an osmolality of from 270 mOsmol/kg to 310 mOsmol/kg.

The advantages of the present invention arise in particular from the following examples.

EXAMPLES

The percentages below are based on the weight (unless expressly stated otherwise).

Example 1

Surface Tension

The aim was to analyse the surface activity of a combination of octenidine and glycerol. For this, 1 part by weight of a composition which consists of 0.5% octenidine, 12.1% glycerol and water as the remainder was diluted to 5 parts by weight with water and the surface tension of the resulting use solution (formulation 1A) was determined. For comparison, the surface tension of a 2.42% strength solution of glycerol in water (formulation 1B) and of water (formulation 1C) was determined.

To determine the surface tension using the method of the hanging drop, the contact angle measuring instrument DSA 10 from Krüss GmbH, Hamburg, Federal Republic of Germany, was used. In this method, a hanging drop is produced using a hollow needle. The drop contour that is formed is dependent on the surface tension and is transferred to the PC via a video camera. Then, by means of the software, a contour is placed around the drop and the surface tension (mN/m) is calculated from the contour.

A needle with an outer diameter of 1.835 mm was used. The following results were obtained (Table 1):

TABLE 1

| Formulation | Octenidine | Glycerol | Water | Surface tension |
| --- | --- | --- | --- | --- |
| 1A | 0.1% | 2.42% | 97.48% | 51.7 mN/m |
| 1B | — | 2.42% | 97.58% | 72.8 mN/m |
| 1C | — | — | 100% | 72.8 mN/m |

Accordingly, an aqueous solution containing 0.1% octenidine exhibits a significantly lower surface tension than an aqueous solution without octenidine.

Example 2

Wetting Effect

As regards the wetting effect, the following were compared:
Octenisept
Ringer's solution and
0.1% octenidine in water In this experiment, raw meat was used as a model for wound and mucosa.

To determine the wetting behaviour, in each case the spraying and rinsing method was tested under conditions simulating those met in practice. For this, pieces of raw meat were wetted on the level and on an incline (ca. 30°) and the run of the liquid or the rinsing-off of residual particles on the surface were assessed macroscopically.

Spraying Method:
The raw meat was sprayed until completely wet using a spray pump and the run-off behaviour was assessed.

Rinsing Method:
Using a disposable pipette, ca. 3 ml were applied and the run-off behaviour was assessed.

Result:
Macroscopically, it was not possible to detect any differences in wetting or cleaning behaviour of the various formulations and/or various methods given above.

Evaluation:
An addition of surfactants such as cocamidopropylbetaine, which is present in Octenisept, is thus not necessary for an antiseptic, in particular a wound and mucosa antiseptic. Evidently, octenidine dihydrochloride, being a quaternary ammonium compound, adequately reduces the surface tension.

Example 3

Osmolality

For this investigation, compositions were prepared which consist of 0.5% octenidine, various amounts of glycerol (%) and water as the remainder (Table 2).

TABLE 2

| Composition | Glycerol | Formulation | Glycerol |
| --- | --- | --- | --- |
| 3A | 10.0% | 3G | 13.0% |
| 3B | 10.5% | 3H | 13.5% |
| 3C | 11.0% | 3I | 14.0% |
| 3D | 11.5% | 3J | 14.5% |
| 3E | 12.0% | 3K | 15.0% |
| 3F | 12.5% | | |

These compositions were diluted with water (1 part by weight to 5 parts by weight), and the osmolality of the resulting use solutions was determined using a semimicro-osmometer from Knauer (Table 3).

TABLE 3

| Solution used | Glycerol | Osmolality | Solution used | Glycerol | Osmolality |
| --- | --- | --- | --- | --- | --- |
| 3A | 2.0%* | 231 mOsmol/kg* | 3G | 2.6%* | 309 mOsmol/kg* |
| 3B | 2.1%* | 240 mOsmol/kg* | 3H | 2.7%* | 317 mOsmol/kg* |
| 3C | 2.2%* | 261 mOsmol/kg* | 3I | 2.8%* | 331 mOsmol/kg* |
| 3D | 2.3%* | 268 mOsmol/kg* | 3J | 2.9%* | 344 mOsmol/kg* |
| 3E | 2.4%* | 287 mOsmol/kg* | 3K | 3.0%* | 351 mOsmol/kg* |
| 3F | 2.5%* | 295 mOsmol/kg* | | | |

*following dilution with water.

Example 4

Stability a) Stability of the Compositions

A composition which consists of 0.5% octenidine, 12.1% glycerol and water as the remainder (formulation 4A) was prepared by mixing said components and investigated with regard to its stability. This composition can be rendered isotonic through dilution with water. For comparison, formulations which consist of 0.5% octenidine, 4.5% sodium chloride and water as the remainder (formulation 4B) or 0.5% octenidine, 4.3% sodium chloride, 0.15% potassium chloride, 0.165% calcium chloride*2H$_2$O and water as the remainder (formulation 4C), and also a formulation of 0.5% octenidine in water (formulation 4D) were prepared and likewise investigated with regard to their stability. The results are shown in Table 4.

TABLE 4

| Formulation | Octenidine | Isotonicity agent | Stability of the concentrate |
| --- | --- | --- | --- |
| 4A | 0.5% | 12.1% glycerol | Stable |
| 4B | 0.5% | 4.5% sodium chloride | Spontaneous formation of |

TABLE 4-continued

| Formulation | Octenidine | Isotonicity agent | Stability of the concentrate |
|---|---|---|---|
| 4C | 0.5% | 4.3% NaCl, 0.15% KCl, 0.165% CaCl$_2$ * 2H$_2$O | crystalline precipitations Spontaneous formation of crystalline precipitations |
| 4D | 0.5% | — | Stable |

Like the composition of 0.5% octenidine in water, the composition which further comprises 12.1% glycerol can also be prepared in the form of an aqueous solution. By contrast, during the preparation of the aqueous compositions which, besides 0.5% octenidine, comprise instead of glycerol (i) sodium chloride or (ii) a mixture of sodium chloride, potassium chloride and calcium chloride in the weight ratio known from Ringer's solution as isotonicity agent, crystals are formed spontaneously. The crystal formation is irreversible.

b) Stability of the Use Solutions 1 part by weight of a composition which consists of 0.5% octenidine, 12.1% glycerol and water as the remainder was diluted to 5 parts by weight with water and the resulting isotonic use solution (290 mOsmol/kg) of 0.1% octenidine and 2.42% glycerol in water was investigated with regard to its stability. For comparison, 0.1% strength aqueous solutions of octenidine rendered isotonic by means of sodium chloride or Ringer's solution (290 mOsmol/kg) were prepared and likewise investigated with regard to their stability. The results are shown in Table 5.

Table 5

| Octenidine | Isotonicity agent | Stability |
|---|---|---|
| 0.1% | 0.85% sodium chloride | Spontaneous formation of crystalline precipitations |
| 0.1% | 99.9% Ringer's solution | Spontaneous formation of crystalline precipitations |
| 0.1% | 2.42% glycerol | Stable between +4° C. and +40° C. |

Aqueous solutions with a content of 0.1% octenidine are accordingly not stable as Ringer's solution and isotonic sodium chloride solution. By contrast, aqueous isotonic octenidine-containing solutions with glycerol are stable.

Example 5

Efficacy when Adding Other Compounds

In a quantitative suspension experiment in accordance with DGHM (status: 1 Sep. 2001, Gebel et al.), the efficacy of various formulations was investigated. In each case, aqueous formulations containing 0.1% octenidine and 1% of the stated surfactant (or 2.42% glycerol) were tested. The investigations were carried out with and without loading. The FCS loading simulates the organic loadings in the wound.

The results show that in aqueous formulations with a content of octenidine with glycerol, the impairment of the biocidal efficacy observed with various surfactants does not occur. This is established to an even more marked degree especially in the case of tests with loading.

| | Surfactant | Without loading | | | | | 10% FCS (foetal calf serum) | | | | |
|---|---|---|---|---|---|---|---|---|---|---|---|
| | | 15 sec | 30 sec | 1 min | 2 min | 3 min | 15 sec | 30 sec | 1 min | 2 min | 3 min |
| | *P. aeruginosa* | | | | | | | | | | |
| 1 | — | 5.61 | 5.72 | 5.62 | 5.69 | 5.71 | 5.60 | 5.80 | 5.85 | 5.88 | 5.84 |
| 2 | 2.42% glycerol | 5.61 | 5.72 | 5.62 | 5.69 | 5.71 | 5.90 | 5.80 | 5.85 | 5.88 | 5.84 |
| 3 | Cocamidopropyldimethylamine oxide | 5.61 | 5.72 | 5.62 | 5.69 | 5.71 | 1.83 | 3.58 | 4.90 | 5.88 | 5.84 |
| 4 | Macrogol glycerol hydroxystearate 40EO | 5.61 | 5.72 | 5.62 | 5.69 | 5.71 | 2.07 | 2.69 | 5.85 | 5.88 | 5.84 |
| 5 | Cocamidopropylbetaine | 5.61 | 5.72 | 5.62 | 5.69 | 5.71 | 0.00 | 0.00 | 0.00 | 0.00 | 0.00 |
| 6 | Sodium cocoamphopropionate | 5.61 | 5.72 | 5.62 | 5.69 | 5.71 | 0.00 | 0.00 | 0.00 | 0.00 | 0.00 |
| 7 | Cocamidopropylhydroxysultaine | 1.41 | 2.46 | 4.51 | 5.69 | 5.71 | 0.00 | 0.00 | 0.00 | 0.00 | 0.00 |
| 8 | Sodium cocoamphoacetate | 0.00 | 0.00 | 1.18 | 1.34 | 1.57 | 0.00 | 0.00 | 0.00 | 0.00 | 0.00 |
| | *S. aureus* | | | | | | | | | | |
| 9 | — | 5.74 | 5.80 | 5.81 | 5.76 | 5.79 | 3.06 | 5.69 | 5.68 | 5.79 | 5.76 |
| 10 | 2.42% glycerol | 5.44 | 5.80 | 5.81 | 5.76 | 5.79 | 3.88 | 5.69 | 5.68 | 5.79 | 5.76 |
| 11 | Cocamidopropyldimethylamine oxide | 3.27 | 5.50 | 5.81 | 5.76 | 5.79 | 2.86 | 4.37 | 5.68 | 5.79 | 5.76 |
| 12 | Macrogol glycerol hydroxystearate 40EO | 3.72 | 4.72 | 5.51 | 5.76 | 5.79 | 5.76 | 5.69 | 5.68 | 5.79 | 5.76 |
| 13 | Cocamidopropylbetaine | 1.77 | 2.69 | 4.81 | 5.46 | 5.79 | 2.51 | 5.69 | 5.68 | 5.79 | 5.76 |
| 14 | Sodium cocoamphopropionate | 2.12 | 4.31 | 5.81 | 5.76 | 5.79 | 2.12 | 4.61 | 5.68 | 5.79 | 5.76 |
| 15 | Cocamidopropylhydroxysultaine | 2.63 | 3.37 | 4.58 | 4.81 | 5.79 | 2.33 | 4.54 | 5.68 | 5.79 | 5.76 |
| 16 | Sodium cocoamphoacetate | 0.00 | 0.00 | 0.00 | 0.00 | 0.00 | 0.00 | 0.00 | 0.00 | 0.00 | 0.00 |
| | *C. albicans* | | | | | | | | | | |
| 17 | — | 4.90 | 4.90 | 4.95 | 5.00 | 4.85 | 4.90 | 4.78 | 4.85 | 4.85 | 4.90 |
| 18 | 2.42% glycerol | 4.90 | 4.90 | 4.95 | 5.00 | 4.85 | 4.90 | 4.78 | 4.85 | 4.85 | 4.90 |
| 19 | Cocamidopropyldimethylamine oxide | 0.78 | 0.85 | 0.99 | 1.36 | 1.30 | 0.60 | 0.53 | 0.64 | 0.85 | 1.02 |
| 20 | Macrogol glycerol hydroxystearate 40EO | 4.12 | 4.90 | 4.95 | 5.00 | 4.85 | 1.43 | 1.57 | 3.31 | 4.85 | 4.90 |
| 21 | Cocamidopropylbetaine | 0.74 | 0.77 | 0.86 | 0.96 | 0.82 | 0.70 | 0.65 | 0.74 | 0.78 | 0.85 |
| 22 | Sodium cocoamphopropionate | 0.56 | 0.61 | 0.83 | 1.03 | 1.04 | 0.57 | 0.70 | 0.77 | 0.81 | 0.88 |
| 23 | Cocamidopropylhydroxysultaine | 0.58 | 0.70 | 0.91 | 0.99 | 0.85 | 0.68 | 0.58 | 0.58 | 0.74 | 0.84 |
| 24 | Sodium cocoamphoacetate | 0.78 | 0.85 | 0.83 | 0.94 | 0.78 | 0.57 | 0.63 | 0.75 | 0.84 | 0.92 |

The invention claimed is:

1. An antimicrobially effective composition comprising for 100% by weight:
   a) between 0.15% and 5% by weight of bispyridinium alkane,
   b) between 5% and 20% by weight of humectant and
   c) Water,
   where the composition:
   is free from surfactant and wherein the composition is free of aliphatic alcohol and aromatic alcohol.

2. The composition according to claim 1, wherein the composition is free from inorganic salts.

3. The composition according to claim 1, wherein the composition is free from antioxidant.

4. The composition according to claim 1, wherein component a) is octenidine dihydrochloride.

5. The composition according to claim 1, wherein the composition comprises 0.2 to 2.5% by weight of component a).

6. The composition according to claim 1, wherein the humectant is selected from the group of polyhydric alcohols selected from the group consisting of glycerol, 1,2-propylene glycol, sorbitol, glucose, fructose, glucuronic acid, lactose, lactic acid, lactates, lactulose, polyethylene glycols, sucrose, hyaluronic acid, xylitol, xylose and mixtures thereof.

7. The composition according to claim 6, wherein component b) is glycerol.

8. The composition according to claim 1, wherein the composition comprises 10 to 15% by weight of component b).

9. The composition according to claim 1, wherein the composition consists of the components:
   a) Octenidine dihydrochloride in an amount of from 0.25 to 1% by weight,
   b) Glycerol in an amount of from 11 to 13% by weight, and
   c) Water as the remainder.

10. A method for the disinfection of injured or uninjured skin of a human being or animal, which comprises applying to the skin an effective amount of a solution comprising, for 100% by weight:
    a) 0.001% to 1% by weight of bispyridinium alkane,
    b) between 5% to 20% by weight of humectants, and
    c) water,
    where the solution:
    (i) has an osmolality of from 230 to 350 mOsmol/kg and
    (ii) is free from surfactant and wherein the composition is free of aliphatic alcohol and aromatic alcohol.

11. The method according to claim 10, characterized in that the disinfection method involves an ultrasound-associated wound treatment (UAW).

12. The method according to claim 10, wherein the injured or uninjured skin is that of a newborn human being or animal.

13. The method according to claim 10, wherein the injured or uninjured skin is that of a premature human being or animal.

* * * * *